US012324935B2

(12) United States Patent
Saenz Julia et al.

(10) Patent No.: US 12,324,935 B2
(45) Date of Patent: Jun. 10, 2025

(54) ULTRASOUND-EMITTING APPARATUS FOR APPLYING SELECTIVE TREATMENTS TO ADIPOSE TISSUE IN BODY REJUVENATION/REMODELLING PROCESSES

(71) Applicant: Jose Manuel Saenz Julia, Fornells de la Selva (ES)

(72) Inventors: Jose Manuel Saenz Julia, Fornells de la Selva (ES); Antonio Fortes Madrigal, Cornella de Llobregat (ES); Oliver Millan Blasco, Sant Just Desvern (ES)

(73) Assignee: Jose Manuel Saenz Julia, Fornells de la Selva (ES)

( * ) Notice: Subject to any disclaimer, the term of this patent is extended or adjusted under 35 U.S.C. 154(b) by 165 days.

(21) Appl. No.: 17/758,845

(22) PCT Filed: Feb. 11, 2021

(86) PCT No.: PCT/ES2021/070099
§ 371 (c)(1),
(2) Date: Jul. 14, 2022

(87) PCT Pub. No.: WO2021/160917
PCT Pub. Date: Aug. 19, 2021

(65) Prior Publication Data
US 2023/0040937 A1    Feb. 9, 2023

(30) Foreign Application Priority Data
Feb. 13, 2020   (ES) ................ ES202030122

(51) Int. Cl.
*A61N 7/02*   (2006.01)
*A61N 7/00*   (2006.01)

(52) U.S. Cl.
CPC ........ *A61N 7/02* (2013.01); *A61N 2007/0004* (2013.01)

(58) Field of Classification Search
CPC ..... A61N 2007/0004; A61N 7/00; A61N 7/02
See application file for complete search history.

(56) References Cited

U.S. PATENT DOCUMENTS 5,902,242 A * 5/1999 Ustuner .............. G01S 7/52074
600/443
2002/0128592 A1 9/2002 Eshel
(Continued)

OTHER PUBLICATIONS

Hirohide Miwa, et al., "Effect of Ultrasound Application on Fat Mobilization", Pathophysiology, vol. 9, pp. 13-19, 2002.
(Continued)

*Primary Examiner* — John D Li
(74) *Attorney, Agent, or Firm* — LUCAS & MERCANTI, LLP (57) ABSTRACT

An ultrasound-emitting apparatus for applying selective treatments to hypodermic tissue (adipose tissue and connective tissue) in body rejuvenation/remodelling processes, by an electric-pulse generator, an ultrasound transducer (3), an electronic control device (6) provided with specific software that controls the frequency, voltage and work cycle of the pulse generator; and application means (4) for orienting and directing the acoustic field on the area of the patient/user to be treated, wherein, in each firing, the transducer emits an acoustic field with an energy density no greater than 0.7 W/cm² and a minimum emission duration of 100 ms. Preferably, the transducer emits either at a single frequency or in a frequency sweep, in a frequency range of 185-333 kHz, and even more preferably at 244 kHz.

10 Claims, 8 Drawing Sheets

(56) References Cited

U.S. PATENT DOCUMENTS

| | | | |
|---|---|---|---|
| 2007/0055154 A1 | 3/2007 | Torbati | |
| 2009/0062724 A1* | 3/2009 | Chen | A61N 7/00 604/22 |
| 2010/0198064 A1 | 8/2010 | Perl et al. | |
| 2014/0257145 A1* | 9/2014 | Emery | A61N 7/00 601/2 |
| 2016/0303402 A1* | 10/2016 | Tyler | A61B 5/0036 |
| 2019/0192875 A1* | 6/2019 | Schwarz | A61N 7/00 |
| 2020/0187907 A1* | 6/2020 | Qiu | B06B 1/0622 |
| 2020/0188696 A1* | 6/2020 | Rousso | A61N 7/00 |

OTHER PUBLICATIONS

Sebastian Mir-Mir M.D., et al., "Efficacy and Safety of Treatment With Focused Ultrasound of High Intensity Y Short Frequency of Emission (Deep Slim®) for the Reduction of Localized Fat" and Machine Translation, 51 pages, 2019.

International Search Report for Corresponding International Application No. PCT/ES2021/070099 dated May 13, 2021 and English Translation, 7 pages.

\* cited by examiner

ULTRASOUND-EMITTING APPARATUS FOR APPLYING SELECTIVE TREATMENTS TO ADIPOSE TISSUE IN BODY REJUVENATION/REMODELLING PROCESSES

CROSS REFERENCE TO RELATED APPLICATION

This application is a 371 of PCT/ES2021/070099, filed on Feb. 11, 2021 which claims the benefit of Spanish Patent Application No. P202030122, filed on Feb. 13, 2020, each of which are incorporated herein by reference.

OBJECT OF THE INVENTION

The invention, as expressed in the title of this specification, relates to an ultrasound-emitting apparatus for applying selective treatments to hypodermic tissue (adipose tissue and connective tissue) in body rejuvenation/remodelling processes, contributing advantages and features that are later described in detail and imply an improvement to the current state of the art to the function for which it is intended.

The object of the present invention lies, specifically, in an apparatus that, suitable for performing body rejuvenation/remodelling processes, comprises an ultrasound transducer that, in addition to an application means, is connected to an electronic device that regulates its electric and acoustic power with the particularity that the acoustic field emitted is a multi-focus ultrasound with a low-intensity acoustic field and low frequency that, with waveforms of variable amplitude, work cycle and frequency, allows it to be selective with the hypodermic tissue, specifically, producing/inducing physiological lipolysis with a structural change of the adipocyte in the adipose cells, reducing the hypertrophic state thereof together with an increase in the density of the hypodermic connective tissue, producing physiological restructuring of the same without cell death, defining what is called an involution in the elastosis of dermo-hypodermic tissue.

FIELD OF APPLICATION OF THE INVENTION

The field of application of the present invention falls within the sector of the industry dedicated to the manufacture of apparatuses intended for performing non-invasive aesthetic/medical treatments and body rejuvenation/remodelling, focusing particularly on the field of those comprising ultrasound technology.

BACKGROUND OF THE INVENTION

As a reference to the current state of the art, it should be noted that although the use of ultrasound technology in cellulite reduction treatments or other non-invasive body remodelling methods is known, the currently existing apparatuses are based on focused ultrasound with a high-intensity acoustic field with the aim of achieving cavitation and cell death (destruction of adipocytes and connective tissue).

The acoustic field generated by the transducer of the ultrasound devices in cellulite treatments or other non-invasive body remodelling methods is generally focused or unfocused.

Figure 9:
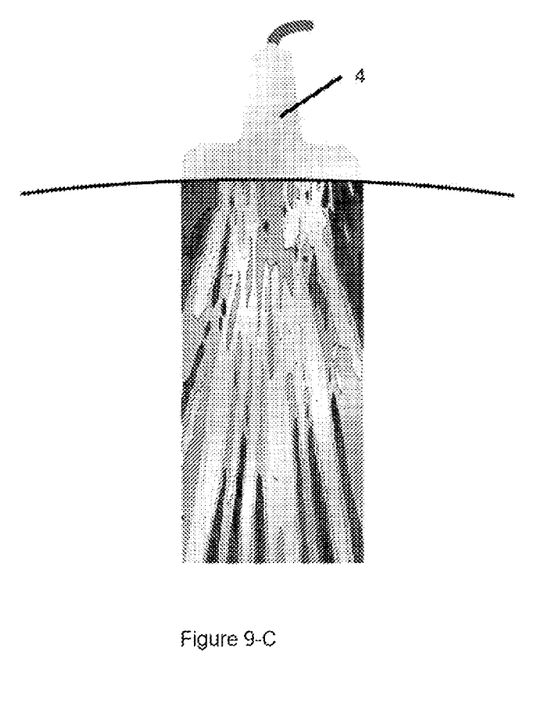

FIG. 9-A shows the radiation map of a focused transducer, where all the energy is spatially concentrated at a point (9) called focus, with the aim of causing lysis and therefore cell death.

Although less common, there are also ultrasound devices in cellulite treatments or other non-invasive body remodelling methods that generate an unfocused acoustic field. FIG. 9-B shows the radiation map of an unfocused transducer. It can be seen that the radiation map thereof is divided into two regions, based on the distance to the transducer (4).

The region closest to the transducer (4) is called the near field or Fresnel region (10). In this region, the acoustic field intensity varies considerably according to distance, as can be seen in the graph of FIG. 9-B.

The region farthest from the transducer (4) is called the far field or Fraunhofer region (11). The beginning of the far field region is defined by the following equation $$N = \frac{D^2}{4\lambda}$$

where N is the distance where the far field region begins, D is the diameter of the ultrasound-generating element or transducer, and $\lambda$ is the wavelength of the ultrasound signal in the tissue.

In this region, the acoustic field intensity is more uniform, but it decreases with distance.

The main drawback of this type of emission is that, in the near field region, radiation is highly irregular and depends on distance, as shown in the graph of FIG. 9-B.

The objective of the present invention is, therefore, the development of an improved apparatus for applying said ultrasound-based treatments which enables improved results to be obtained without cell death and without the risk of burns, since it is an emitting device with a low-intensity acoustic field. This is due to the precise regulation of the transducer thereof, and it should be noted that the existence of any other apparatus or any other invention of similar application, which has technical and constitutive features that are the same or similar to those specifically had by the apparatus claimed herein, is unknown at least to the applicant. In other words, a multi-focus device, preferably with a low-intensity acoustic field and low emission frequency without cavitation phenomenon or hyperthermia or hypothermia.

DESCRIPTION OF THE INVENTION

The ultrasound-emitting apparatus for applying selective treatments to hypodermic adipose tissue in body rejuvenation/remodelling processes that the invention proposes is configured as the ideal solution for the aforementioned objective, wherein the characterising details that make it possible and conveniently distinguish it are included in the final claims accompanying this description.

More specifically, what the invention proposes, as noted above, is a suitable apparatus for performing rejuvenation/remodelling processes which comprises:

an electric-pulse generator
an ultrasound transducer (3),
an electronic control device (6) provided with specific software that controls the frequency, voltage and work cycle of the pulse generator
application means (4) for orienting and directing the acoustic field on the area of the patient/user to be treated, The ultrasound-emitting apparatus for applying selective treatments to hypodermic tissue (adipose tissue and connective tissue) in body rejuvenation and/or remodelling processes object of the invention is characterised in that the acoustic field generated by the transducer is multi-focus.

FIG. 9-C shows a radiation field produced by a multi-focus transducer, where the existence of multiple radiation foci and how said foci alternate with regions of low acoustic pressure is observed. The advantages of this novel mode of emission are:

- The multiple emission foci range from the epidermis to the hypodermis, acoustically affecting all layers of the skin. The multi-focus beam distributes energy over a region wider than the focused beam (FIG. 9-A) and wider than the unfocused beam (FIG. 9-B), both in terms of depth and width, affecting a greater volume of tissue and therefore reducing the energy density captured by one same tissue, thus avoiding burns, increasing the physiological metabolism of the adipose and connective tissue by entering into mechanical resonance without thermal effects with said tissues, and inhibiting cell adaptation and saturation of the same.
- The multi-focus acoustic field allows working on localised oedematous fat in large areas such as, for example, the abdomen or thighs, hips, knees, arms, trochanter, etc., and treating soft cellulite in practically all stages thereof, improving the appearance of the skin.
- With multi-focus emission, it is possible to volumetrically vary the adaptation of the tissue to avoid saturation of mechanosensitive cells (integrins, ligands, RAC1, Rho, etc.). Therefore, if the emission were homogeneous, tissue saturation would occur, thereby reducing the clinical effect.
- By having a multi-focus beam, in other words, acoustic pressure regions alternating with other low-pressure regions, metabolic stress is reduced, thus favouring the permeability of the cell membrane (enhancing the phenomenon of lipolysis), increasing fibroblast activity, etc.

In each firing, the device emits an acoustic field with an acoustic field intensity no greater than 0.7 W/cm$^2$ and a minimum temporary emission duration of 100 ms, producing or inducing physiological lipolysis with a structural change of the adipocyte in hypodermic tissue (adipose tissue and connective tissue), reducing the hypertrophic state thereof together with an increase in the density of the hypodermic connective tissue, producing physiological restructuring of the same without cell death, defining what is called an involution in elastosis or ageing of the dermo-hypodermic tissue.

The way in which the apparatus of the invention delivers energy produces mechanical resonance through which a process for rejuvenating demo-hypodermic structures (adipose tissue and connective tissue) is achieved without the cavitation effect or the destruction of tissue. This represents an alternative in effective non-invasive liposculpture with no side effects, which works in the deepest layer of the skin, involuting the state of elastosis of the tissues, rejuvenating the state thereof thanks to its technology for applying multi-focus ultrasound with a low-intensity acoustic field and low frequency, which, likewise, also provides excellent results by compacting tissue, remodelling the silhouette, and stimulating the production of collagen in the hypodermis, without pain or side effects. With this acoustic field intensity, a mechanical index of less than 0.5 is guaranteed, through which cavitation cannot be generated.

Preferably, the frequency of the electrical signal delivered to the transducer is comprised in the range of 185-333 kHz. This frequency range covers the 5th harmonic of the 37 kHz frequency and the 7th harmonic of the 45 kHz frequency. Given that the range of 37-45 kHz is the one in which the adipocytes have their resonance frequency (depending on the diameter thereof), which causes the adipocytes to resonate, but with a lower energy than that which would be obtained in the range from 37 kHz to 45 kHz, the absence of gas bubble formation or explosion is ensured, thus avoiding the phenomenon of cavitation and an increase in the skin's surface temperature. By varying the frequency of the electrical signal delivered to the transducer, the depth of the region of maximum acoustic field intensity varies.

Figure 2:
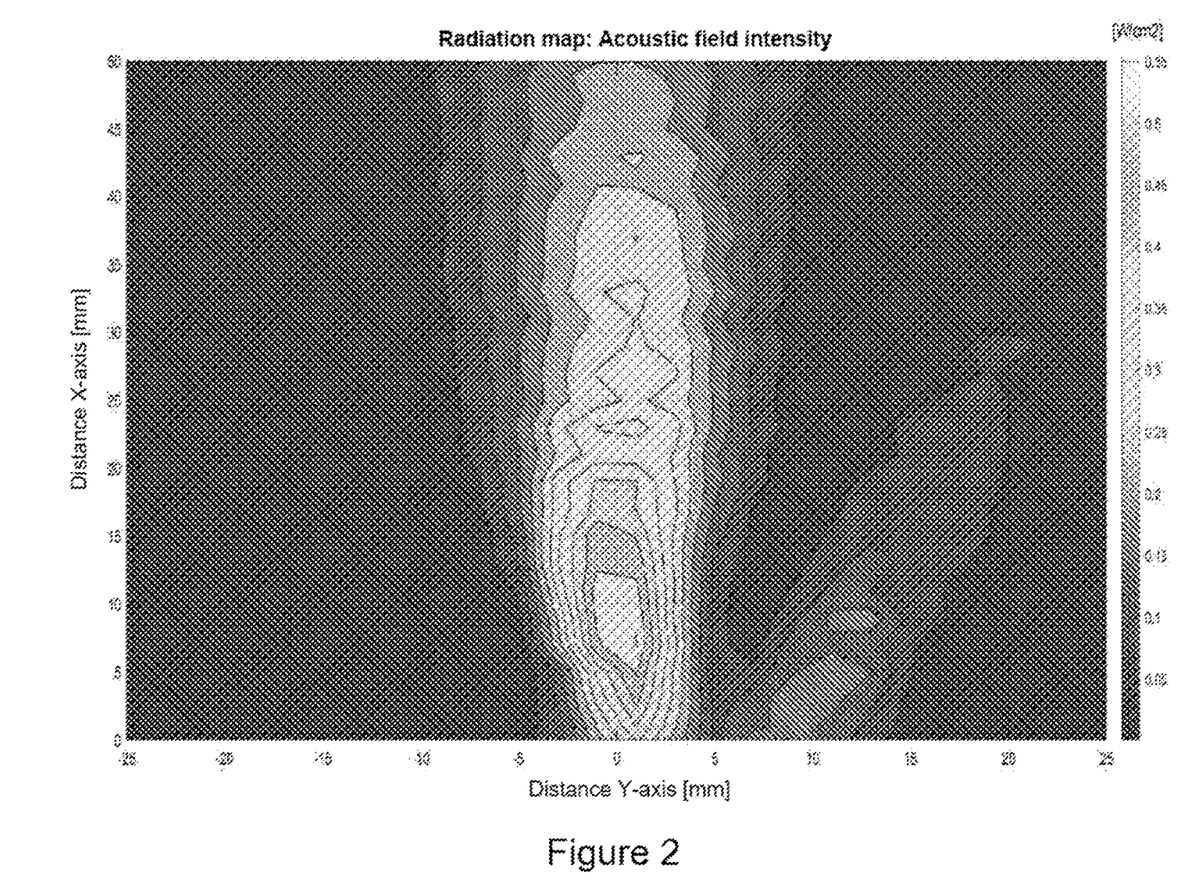
FIG. 2 shows, in a graph of Cartesian axes, the radiation map or acoustic pressure field radiated by the transducer of the apparatus, according to the invention, excited with a frequency of 224 kHz and an acoustic field intensity of less than 0.7 W/cm$^2$, representing a cross-section of 50×50 mm with a resolution of 2 mm.
Figure 3:
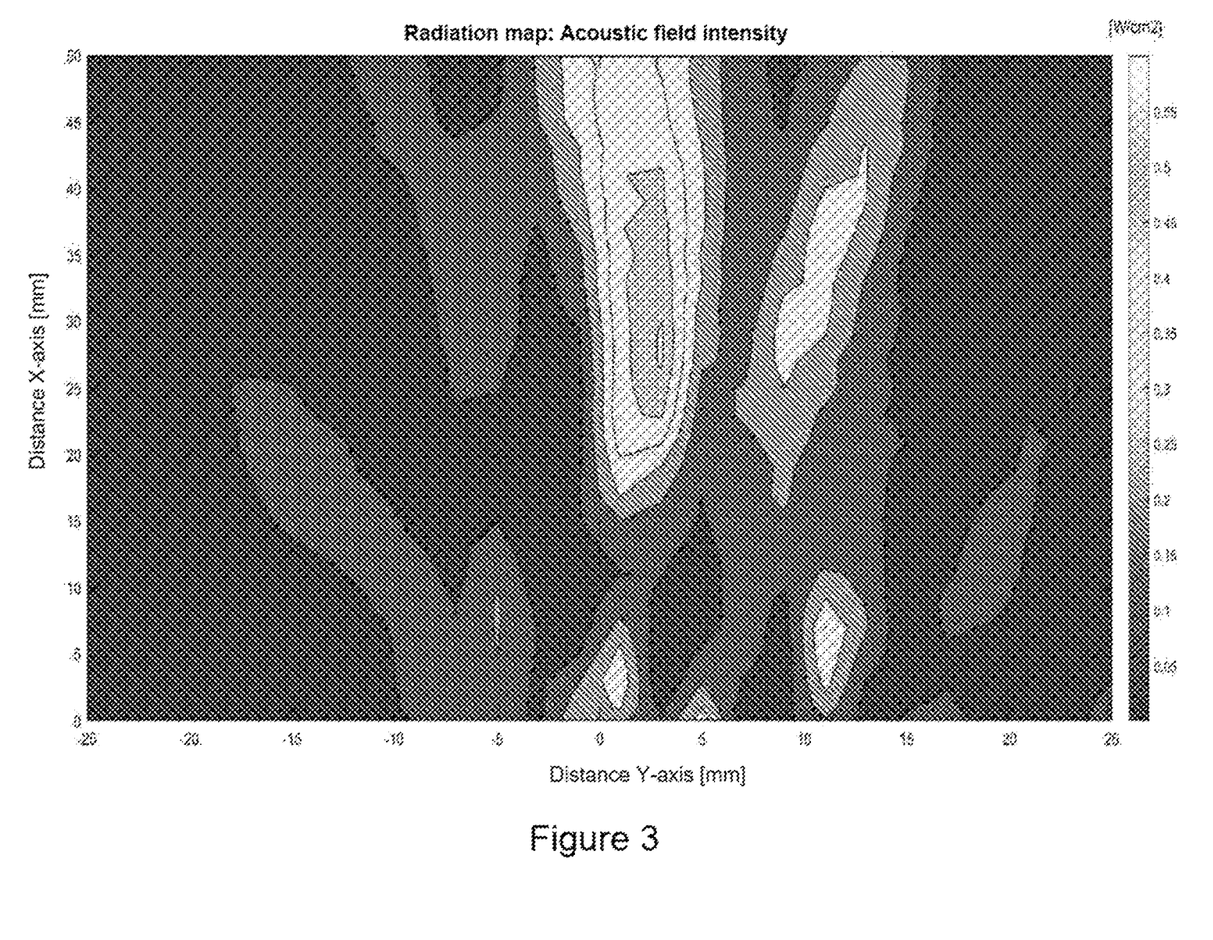
FIG. 3 shows another graph of the map of acoustic pressure radiated by the transducer of the apparatus of the invention, in this case, excited with a frequency of 333 kHz and an acoustic field intensity of less than 0.7 W/cm$^2$, representing a cross-section of 50×50 mm with a resolution of 2 mm.

By way of example, and as shown in FIGS. 2 and 3, when a frequency of 224 kHz is delivered to the transducer, the region of maximum acoustic field intensity is found at a depth between 3 and 20 mm, whereas when a frequency of 333 kHz is delivered to the transducer, the focus moves to a depth between 20 and 50 mm.

By varying the frequency delivered to the transducer, the depth of the focus varies and it is possible to cover a wide variety of therapeutic treatments such as the following:

- between 0.5 mm-15 mm (areolar layer, always depending on the thickness of each patient) cellulite and connective tissue compaction.
- between 15 mm-30 mm (lamellar layer, always depending on the thickness of each patient) localised fat and connective tissue compaction. Two preferred modes of operation are envisaged.

The first mode of operation consists of exciting the transducer at a single frequency, with the aim of selectively affecting adipocytes of a certain diameter. By varying the frequency delivered to the transducer, the user can vary the acoustic distribution of the ultrasound beam and the focus distance (where a greater portion of the energy is concentrated). This enables the device to be adapted to different treatments depending on the depth of the focus. Preferably, the frequency of this first mode of operation is 224 kHz, which allows for the selective treatment of adipocytes with the most common diameter in hypodermic tissue, with total control and the absence of side effects on other tissues. More specifically, said frequency of the acoustic field that is provided by the transducer causes mechanical resonance of the adipose tissue without cavitation effects or hyperthermia or hypothermia.

The second mode of operation consists of exciting the transducer with a "chirp" signal, which is a variable frequency signal that sweeps the range of interest between 185 kHz-333 kHz. By means of this mode of operation, it is possible to attack adipocytes of any diameter, wherein this mode is a technological innovation of this inventive apparatus and it provides important advantages with respect to the devices of the competition.

Preferably, after each burst ("on" time) of the emitting apparatus, there is a rest time ("off" time). Burst is understood as an on-time in which a pulse wave is being emitted, the number of pulses of which depends on the on-time and the frequency of said wave, according to the following equation:

$$n = T\text{on} * f$$

Where n refers to the number of pulses and f refers to the frequency of the burst. The off-time in each firing (sum of rest times after each burst) is at least 200 ms. This off-time is much longer than the time used in devices available on the market, where the off-time thereof does not exceed 20 ms. This longer off-time, compared to those of the competition, allows the circulatory system to evacuate the heat produced by the mechanical movement of the adipocytes when they are affected by the ultrasound beam.

Figure 6:
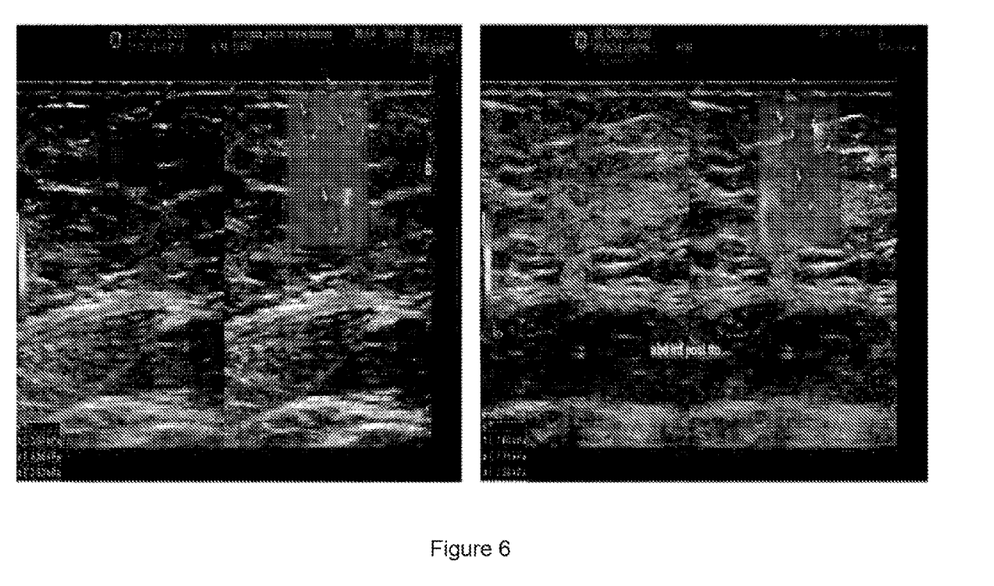
FIG. 6 shows ultrasound imaging where the image on the left shows the state of the hypodermic tissue of the lower abdomen, wherein the fibres of the connective tissue (in white) and the adipose tissue (in black) with a thickness ranging from 0.5 mm (deep dermis) to practically 30 mm (deep fascia) is observed. One hour after treatment, the image on the right shows the effect of the technology, causing generalised compaction of the hypodermic tissue, wherein a greater amount of connective tissue (in white) and redensification of the adipose tissue (between grey and black) is observed, which will lead to the aforementioned tissue changes.
Figure 7:
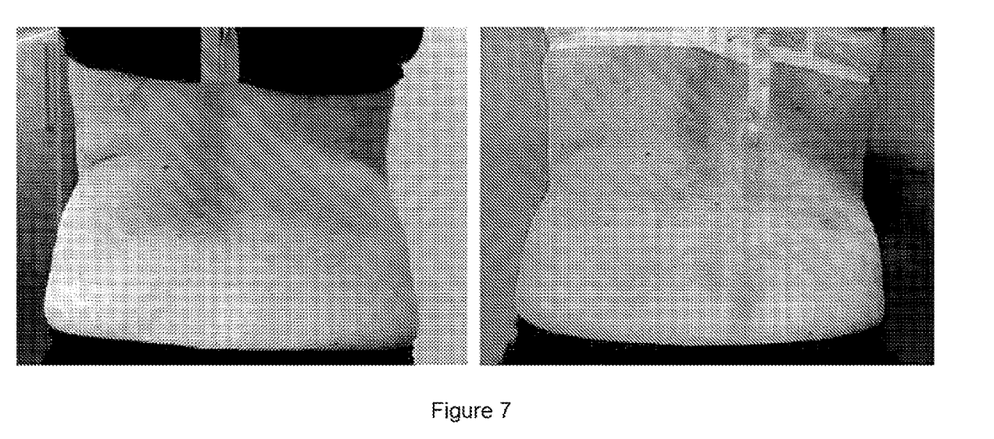
FIG. 7 shows, in the photo on the left, a patient prior to treatment with the technology, where the fat accumulation and the marking of the folds in the lower area of the back due to the inconsistency of the connective tissue caused by the weight of adipose tissue can be seen. In the photo on the right, one month after the photo on the left, the same patient (recognised by the multiple naevi on her back) is shown with an evident reduction in fat accumulation in the lower area of the back, as well as a very significant reduction in the very folds of the treated area due to the compaction of the connective tissue.
Figure 8:
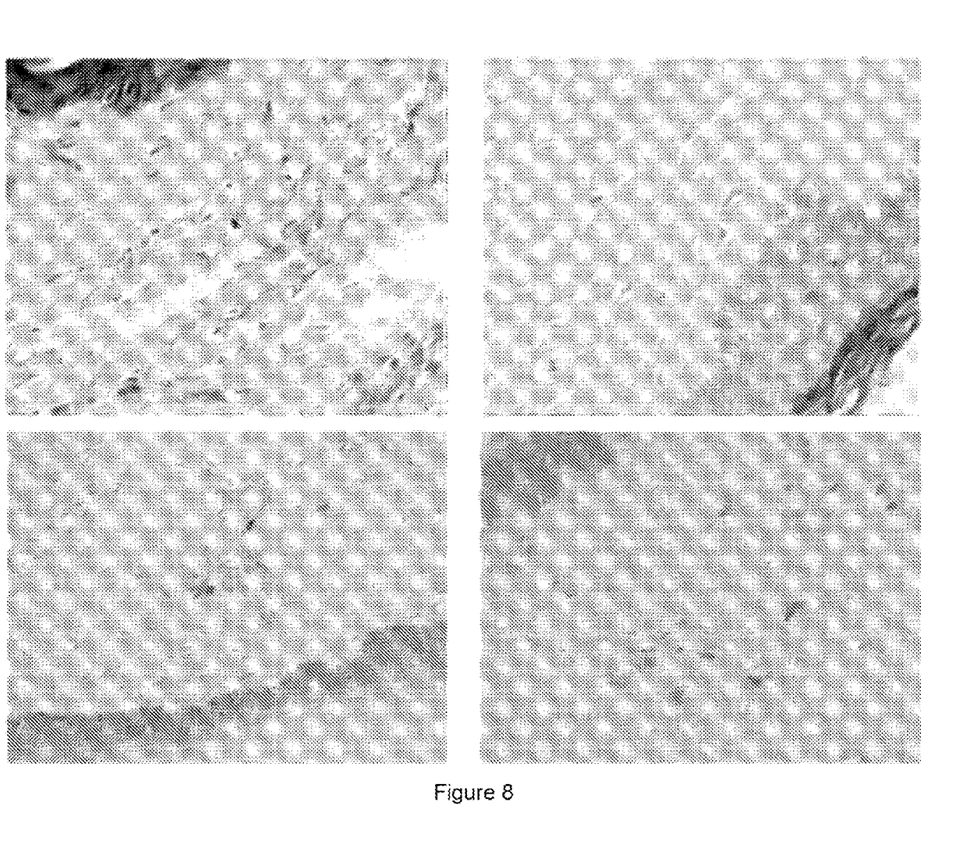
FIG. 8 shows histopathology performed using Masson's Trichrome and 6 immunohistochemical markers (CD64, CD44, CD34, S100, Factor VIII and Alpha Actin) carried out on a skin spindle prior to treatment with the technology (image on the left) and 14 days after treatment with the technology (image on the right).

Preferably, the emitting apparatus performs firing with a duration of 2 seconds with a total of 10 ultrasound bursts. Firing is understood as a series of bursts together with the rest times or off-times thereof between the bursts. This type of excitation guarantees a minimum number of mechanical movements on the adipocytes that induce physiological lipolysis with a structural change of the adipocytes, reducing the hypertrophic states thereof together with an increase in the density of the hypodermic connective tissue, producing physiological restructuring of the same without cell death, defining what is called an involution in the elastosis or ageing of the dermo-hypodermic tissue. In FIGS. 6, 7 and 8, the effects obtained with the apparatus of the invention can be seen.

There are, among others, two possible alternatives to generate a multi-focus acoustic field.

The first involves using a transducer with more than one piezoelectric element.

The second alternative involves inducing a lack of radiation symmetry in a single piezoelectric element by means of non-homogeneous bonding between the piezoelectric element and the casing that form the transducer to guarantee only a finite series of radiation patterns (optimised to have clinical results), and using the chirp signal which makes it possible to vary the generation and composition of standing waves on the surface of the transducer casing, making it vibrate in different modes of vibration, causing the radiation pattern to change in each firing as the chirp frequency increases, producing an effect similar to that of the transducer rotating, but without the need to rotate it. Achieving greater efficiency, since a larger region is insonated, and generating an acoustic signal in the range of (185 kHz-333 kHz) in turn causes the adipocytes to vibrate in a single firing regardless of their diameter.

In short, the apparatus proposed by the present invention, thanks to the aforementioned emission of the multi-focus ultrasound beam and, preferably, its particular combination of low-intensity acoustic field (less than 0.7 W/cm$^2$) and low frequency (range of 185-333 kHz), which represents an innovation for reducing, compacting and eliminating localised fat, allows for total control of the depth of the energy reservoir and selectivity of the target tissue or tissue to be treated by adjusting the emission frequency, all without causing pain or side effects.

DESCRIPTION OF THE DRAWINGS

As a complement to the present description, and for the purpose of helping to make the features of the invention more readily understandable, said description is accompanied by a set of drawings constituting an integral part of the same, which by way of illustration and not limitation represent the following.

From these images of the hypodermic tissue, the following conclusions can be drawn.

Dermis:
  Notable decrease in macromatic elastotic fibres (tissue rejuvenation).

Hypodermis:
  No solution of continuity (lesion) is observed in the adipocyte membranes
  No contribution of macrophages is observed in the analysed area, meaning there is no coagulative necrosis (there is no lesion)
  No vascular lesion is observed
  A reduction (atrophy/involution) in the morphology of the adipose tissue to its physiological state (from a hypertrophic state to a more physiological state) is observed
  Compaction of the adipose tissue and the connective tissue is observed FIGS. 9-A, 9-B and 9-C show the radiation or beam patterns of a focused ultrasound transducer (FIG. 9-A), unfocused ultrasound transducer (FIG. 9-B) and multi-focus ultrasound transducer (FIG. 9-C).

PREFERRED EMBODIMENT OF THE INVENTION

Figure 1:
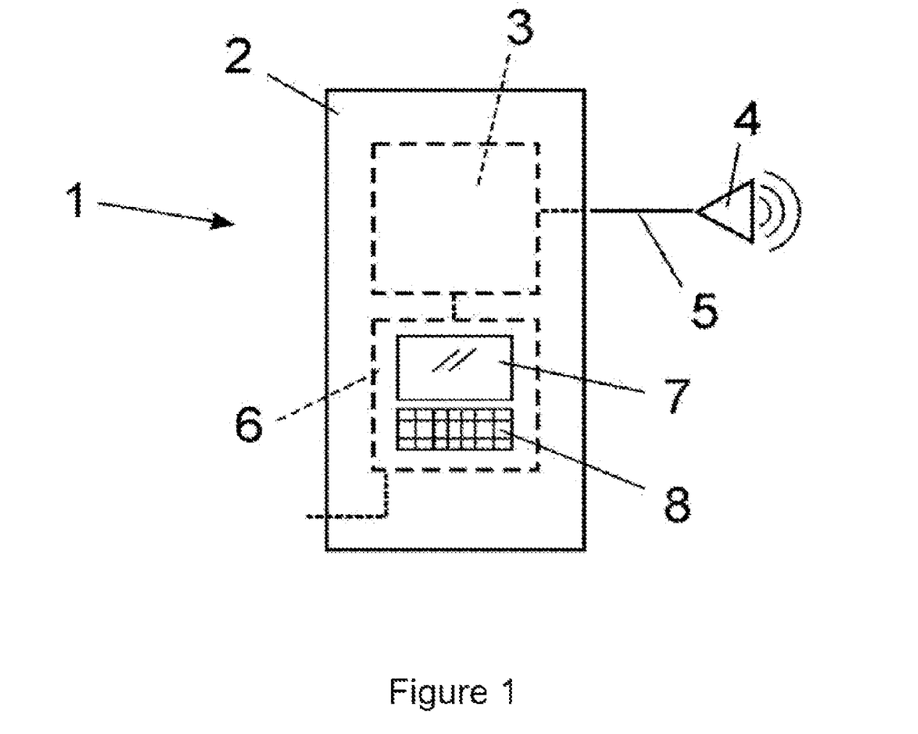
FIG. 1 shows a schematic representation of an example of the ultrasound-emitting apparatus object of the invention, showing the main parts it comprises.

Thus, according to the schematic representation of FIG. 1, the apparatus (1) in question is one of those that essentially comprises, conveniently housed in a protective support structure (2), at least one ultrasound transducer (3) associated with application means (4) for orienting and directing the acoustic field on the area of the patient/user to be treated, with which it is preferably connected via a connection cable (5), and an electronic control device (6) which, conveniently provided with specific software, and via a screen (7) and/or a keyboard (8), allows its operation to be controlled to regulate the acoustic field intensity, the work cycle and excitation frequencies of said transducer (3).

The ultrasound-emitting apparatus for applying selective treatments to hypodermic tissue (adipose tissue and connective tissue) in body rejuvenation and/or remodelling processes object of the invention is characterised in that the acoustic field generated by the transducer (3) is a multi-focus acoustic field.

In a preferred embodiment, the transducer (3) emits an ultrasound beam with a low-intensity acoustic field (less than 0.7 W/cm$^2$) and low frequency, of 185 kHz-333 kHz, with 224 kHz being a commonly used frequency for single emission frequency treatments.

To demonstrate the effectiveness of said apparatus/technology for the aforementioned treatment, different clinical tests, such as ultrasound imaging, clinical photography and histopathology, FIGS. 6, 7 and 8 respectively, and a detailed study of the characterisation of the acoustic field of the transducer under the aforementioned conditions have been carried out, which, after conducting electrical and acoustic radiation tests, provides the following results:

For electrical measurement, an oscilloscope is connected to the terminals of the transducer using a ×10 splitter probe. To gain access to the transducer terminals, the device was opened and 50 cm-long extension cables were connected to the terminals of the power PCB output strip.

The firing of the oscilloscope is set to perform a single sweep and then several bursts are fired and recorded with different settings on the device's control panel.

As a result, the following values of the operating parameters are determined:

Each time the firing button located on the transducer is pressed, 10 bursts of transducer excitation voltage are produced, with a repetition time of 200 ms.

The amplitude of the excitation voltage is 177 Vrms, which generates an ultrasound beam in the transducer with an acoustic field intensity of less than 0.7 W/cm$^2$.

The duration of the bursts varies according to the value adjusted on the device's control panel. This value indicates the duration, in ms, of each burst.

Figure 4:
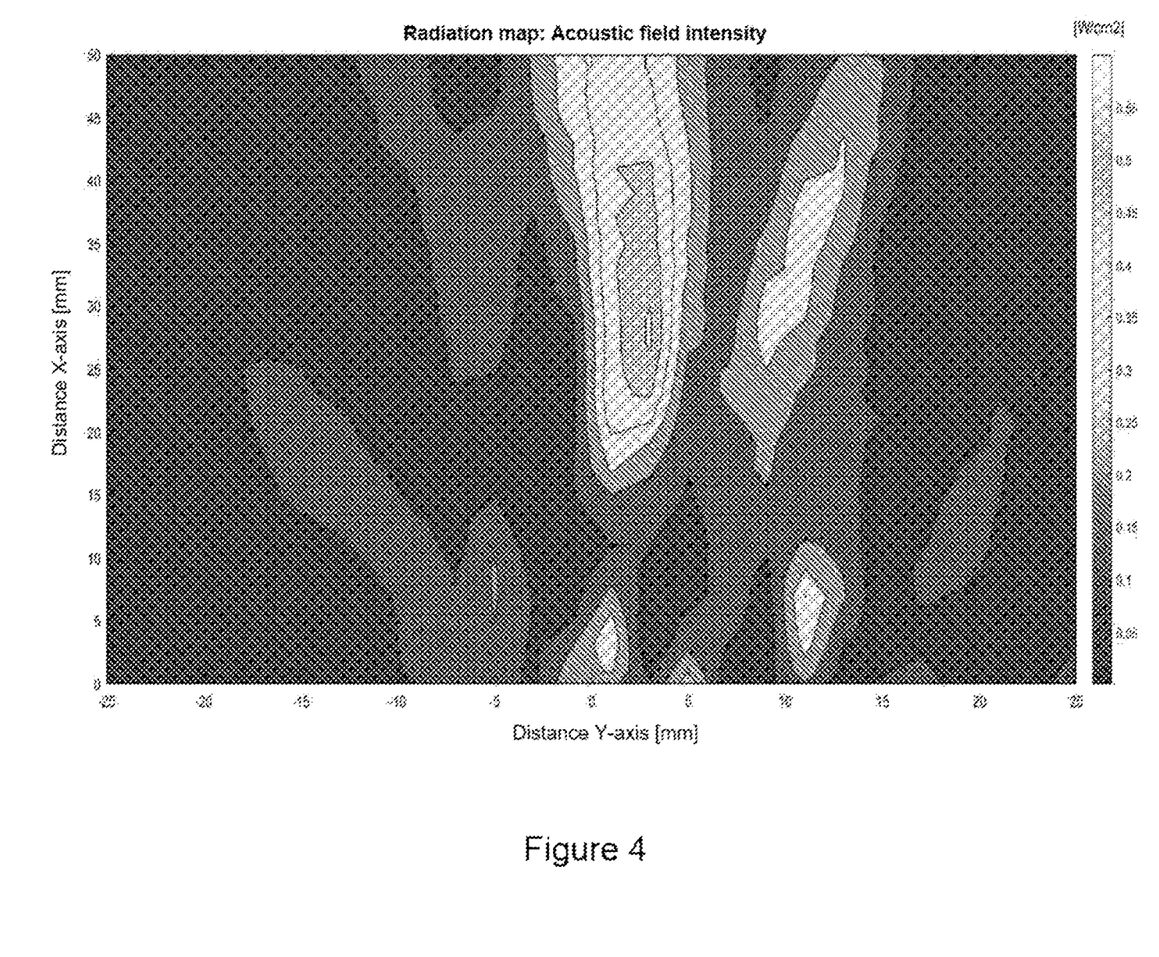
FIG. 4 shows the graph of Cartesian axes with a resolution of 2 mm and the mechanical index calculated from the radiation pattern emitted by the transducer of the apparatus, according to the invention, for a frequency of 224 kHz and an acoustic field power of less than 0.7 W/cm$^2$.
Figure 5:
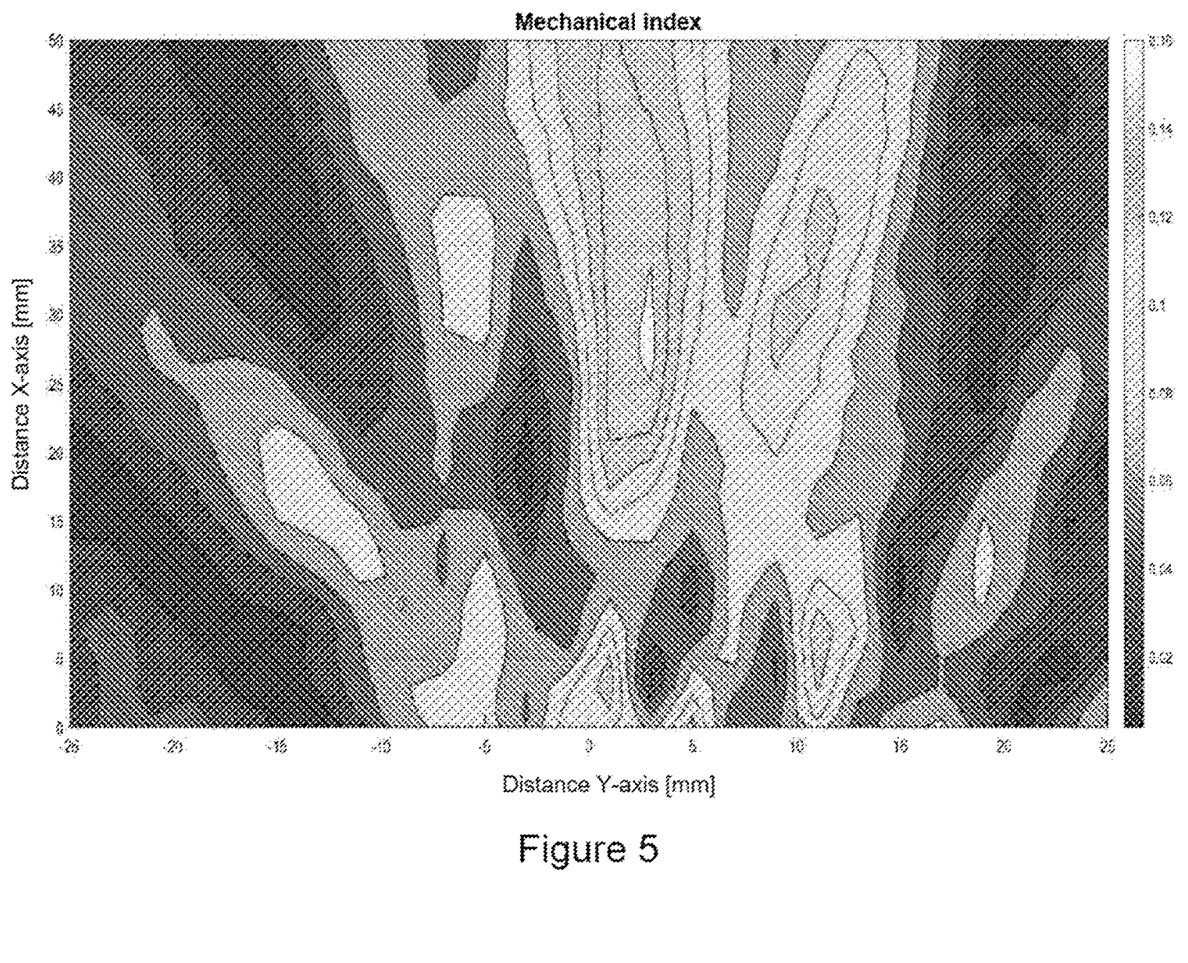
FIG. 5 again shows a graph of Cartesian axes with a resolution of 2 mm and the mechanical index calculated from the radiation pattern emitted by the transducer of the apparatus, according to the invention, for a frequency of 330 kHz and an acoustic field power of less than 0.7 W/cm$^2$.

To verify that the apparatus of the invention does not produce cavitation, the mechanical index (MI) of the radiation patterns shown in FIGS. 2 and 3 has been calculated, giving FIGS. 4 and 5. This index has been calculated using the equation shown below:

$$MI = \frac{P}{\sqrt{f}}$$

Where P is the negative acoustic pressure peak in MPa and f is the centre frequency of the excitation signal of the ultrasound transducer in Mhz. Therefore, according to reference [1], if MI is less than 0.5, cavitation does not occur. As can be seen in FIGS. 4 and 5, this index is less than 0.2, thus guaranteeing that the apparatus of the invention does not produce cavitation.

Acoustic field radiation measurements have been taken by coupling the transducer to be characterised to the side of a test tank filled with water. The acoustic energy propagates from the transducer to the inside of the tank, in the form of an acoustic field that is measured point by point by a hydrophone that moves inside the tank by means of a robotic mechanism.

The measurements are taken at low power, applying a peak voltage of 40 V to the transducer and scaling the obtained measurements to the equivalent values that would be obtained with the nominal voltage of 177 V rms.

A computer with its own program is responsible for moving the transducer and acquiring the value of the acoustic field at each of the programmed points where the hydrophone stops to take the measurement.

Measurements are first taken at a nominal frequency of 224 kHz, starting with a measurement in a region of 50×50 mm, with a resolution of 2 mm, in the horizontal plane that contains the axis of the transducer. FIG. 2 shows the acoustic field intensity (W/cm$^2$) of the ultrasound beam radiated by the transducer of the apparatus excited with a frequency of 224 kHz and an acoustic field intensity of less than 0.7 W/cm$^2$.

The acoustic field measurement has been repeated at the frequency of 333 kHz, giving FIG. 3.

The recorded data is stored forming a matrix that is processed and transformed using commercial software called MatLab® (abbreviation for MATrix LABoratory, consisting of a numerical computation system that offers an integrated development environment with its own programming language).

On the measurements of acoustic radiation diagrams:
By means of controlled non-homogeneous bonding, a lack of radiation symmetry is induced, achieving a phenomenon of multi-focalisation of the ultrasound beam, which can vary in form by adjusting the emission frequency. As can be seen in FIGS. 2 and 3, by varying the excitation frequency from 224 kHz to 333 kHz, the region of maximum acoustic field intensity has varied from a region with a depth between 3 and 20 mm, for the emission frequency of 224 kHz, to a depth between 20 and 50 mm for the frequency of 333 kHz. In this way, it is possible to perform different treatments based on the emission frequency.

Having sufficiently described the nature of the present invention, as well as an example of its implementation, it is not considered necessary to further explain it so that any person skilled in the art may understand its scope and the advantages derived from it.

The invention claimed is:
1. An ultrasound-emitting apparatus for applying selective treatments to hypodermic tissue in body rejuvenation and/or remodelling processes, which comprises,
an electric-pulse generator,
an ultrasound transducer adapted to generate an acoustic field, and
an electronic control device provided with specific software that controls a frequency, a voltage and work cycle of the electric-pulse generator,
wherein the acoustic field generated by the transducer is a multi-focus acoustic field; and
wherein the ultrasound transducer emits at least one firing comprising a plurality of bursts, each burst comprising a plurality of electric pulses, wherein each firing lasts 2 seconds with a total of 10 bursts.

2. The ultrasound-emitting apparatus for applying selective treatments to hypodermic tissue in body rejuvenation and/or remodelling processes, according to claim 1, wherein the ultrasound transducer emits at least one firing comprising a plurality of bursts, each burst comprising a plurality of electric pulses, wherein in each firing, said transducer generates the acoustic field with an energy density no greater than 0.7 W/cm$^2$ and a minimum temporary emission duration of 100 ms.

3. The ultrasound-emitting apparatus for applying selective treatments to hypodermic tissue in body rejuvenation and/or remodelling processes, according to claim 1, wherein said transducer emits in a frequency range of 185-333 kHz.

4. The ultrasound-emitting apparatus for applying selective treatments to hypodermic tissue in body rejuvenation and/or remodelling processes, according to claim 1, wherein the transducer emits at a single frequency.

5. The ultrasound-emitting apparatus for applying selective treatments to hypodermic tissue in body rejuvenation and/or remodelling processes, according to claim 4, wherein the transducer emits at a frequency of 224 kHz.

6. The ultrasound-emitting apparatus for applying selective treatments to hypodermic tissue in body rejuvenation and/or remodelling processes, according to claim 1, wherein the ultrasound transducer emits at least one firing comprising a plurality of bursts, each burst comprising a plurality of electric pulses, wherein the transducer emits at a frequency that varies throughout a single firing, sweeping the range of 185-333 kHz.

7. The ultrasound-emitting apparatus for applying selective treatments to hypodermic tissue in body rejuvenation and/or remodelling processes, according to claim 1, wherein the ultrasound transducer emits at least one firing comprising a plurality of bursts, each burst comprising a plurality of electric pulses, wherein between consecutive bursts there is a rest time, wherein a sum of rest times in a single firing equals or exceeds 200 ms.

8. The ultrasound-emitting apparatus for applying selective treatments to hypodermic tissue in body rejuvenation and/or remodelling processes, according to claim 1, wherein a bonding between a piezoelectric element and a casing that form the transducer is not homogeneous.

9. The ultrasound-emitting apparatus for applying selective treatments to hypodermic tissue in body rejuvenation and/or remodelling processes, according to claim 1, wherein a chirp signal is used which makes it possible to vary the generation and composition of standing waves on the surface of a transducer casing.

10. The ultrasound-emitting apparatus for applying selective treatments to hypodermic tissue in body rejuvenation and/or remodelling processes, according to claim 1, wherein the transducer comprises more than one piezoelectric element.

* * * * *